(12) United States Patent
Burnett et al.

(10) Patent No.: US 8,100,880 B2
(45) Date of Patent: Jan. 24, 2012

(54) AUTOMATED THERAPY SYSTEM AND METHOD

(75) Inventors: Daniel Rogers Burnett, San Francisco, CA (US); Gregory Hall, Redwood City, CA (US); Christopher Hermanson, Santa Cruz, CA (US); Amit Rajguru, Orinda, CA (US)

(73) Assignee: Velomedix, Inc., Menlo Park, CA (US)

( * ) Notice: Subject to any disclaimer, the term of this patent is extended or adjusted under 35 U.S.C. 154(b) by 209 days.

(21) Appl. No.: 12/098,365

(22) Filed: Apr. 4, 2008

(65) Prior Publication Data
US 2008/0262418 A1    Oct. 23, 2008

Related U.S. Application Data

(60) Provisional application No. 60/921,974, filed on Apr. 5, 2007.

(51) Int. Cl.
*A61M 31/00* (2006.01)
(52) U.S. Cl. .......................................... 604/503; 604/66
(58) Field of Classification Search .................. 604/503, 604/508
See application file for complete search history.

(56) References Cited

U.S. PATENT DOCUMENTS

| | | |
|---|---|---|
| 2,078,786 A | 4/1937 | Wood |
| 3,042,042 A | 7/1962 | Blanck |
| 3,505,988 A | 4/1970 | Deane |
| 3,698,396 A | 10/1972 | Katerndahl et al. |
| 3,927,980 A | 12/1975 | Leonard |
| 4,356,826 A | 11/1982 | Kubota |
| 4,413,633 A | 11/1983 | Yanda |
| 4,445,500 A | 5/1984 | Osterholm |
| 4,450,841 A | 5/1984 | Osterholm |
| 4,497,324 A | 2/1985 | Sullivan et al. |
| 4,535,773 A | 8/1985 | Yoon |
| 4,813,429 A | 3/1989 | Eshel et al. |
| 4,883,459 A | 11/1989 | Calderon |
| 4,904,237 A | 2/1990 | Janese |
| 4,963,130 A | 10/1990 | Osterholm |

(Continued)

FOREIGN PATENT DOCUMENTS

GB    2267829 A    12/1993

(Continued)

OTHER PUBLICATIONS

Polderman, K.H., R.T.T. Joe, S.M. Peerdeman, W.P. Vandertop, and A.R.J. Girbes. (2002) Effects of therapeutic hypothermia on intracranial pressure and outcome in patients with severe head injury. Intensive Care Med 28: 1563-1573.*

(Continued)

*Primary Examiner* — Nicholas Lucchesi
*Assistant Examiner* — Jenna Zhang
(74) *Attorney, Agent, or Firm* — Shay Glenn LLP

(57) ABSTRACT

An automated therapy system having an infusion catheter; a sensor adapted to sense a patient parameter; and a controller communicating with the sensor and programmed to control flow output from the infusion catheter into a patient based on the patient parameter without removing fluid from the patient. The invention also includes a method of controlling infusion of a fluid to a patient. The method includes the following steps: monitoring a patient parameter with a sensor to generate a sensor signal; providing the sensor signal to a controller; and adjusting fluid flow to the patient based on the sensor signal without removing fluid from the patient.

7 Claims, 3 Drawing Sheets

U.S. PATENT DOCUMENTS

| | | | |
|---|---|---|---|
| 5,122,267 A | 6/1992 | Giovanetti et al. |
| 5,141,492 A | 8/1992 | Dadson et al. |
| 5,141,493 A | 8/1992 | Jacobsen et al. |
| 5,149,321 A | 9/1992 | Klatz et al. |
| 5,245,367 A | 9/1993 | Miller et al. |
| 5,249,585 A | 10/1993 | Turner et al. |
| 5,344,136 A | 9/1994 | Capdeboscq |
| 5,354,277 A | 10/1994 | Guzman et al. |
| 5,380,160 A | 1/1995 | Chen |
| 5,478,329 A | 12/1995 | Ternamian |
| 5,554,280 A | 9/1996 | Loehr |
| 5,562,821 A | 10/1996 | Gutierrez-Collazo |
| 5,665,227 A | 9/1997 | Watt |
| 5,693,017 A | 12/1997 | Spears et al. |
| 5,709,654 A | 1/1998 | Klatz et al. |
| 5,709,661 A | 1/1998 | Van Egmond et al. |
| 5,730,720 A | 3/1998 | Sites et al. |
| 5,752,929 A | 5/1998 | Klatz et al. |
| 5,755,756 A | 5/1998 | Freedman, Jr. et al. |
| 5,837,003 A | 11/1998 | Ginsburg |
| 5,916,153 A | 6/1999 | Rhea, Jr. |
| 6,019,729 A | 2/2000 | Itoigawa et al. |
| 6,019,783 A | 2/2000 | Philips et al. |
| 6,066,163 A | 5/2000 | John |
| 6,117,076 A | 9/2000 | Cassidy |
| 6,126,684 A | 10/2000 | Gobin et al. |
| 6,146,411 A | 11/2000 | Noda et al. |
| 6,149,624 A | 11/2000 | McShane |
| 6,149,670 A | 11/2000 | Worthen et al. |
| 6,165,207 A | 12/2000 | Balding et al. |
| 6,175,688 B1 | 1/2001 | Cassidy et al. |
| 6,188,930 B1 | 2/2001 | Carson |
| 6,197,045 B1 | 3/2001 | Carson |
| 6,231,594 B1 | 5/2001 | Dae |
| 6,254,567 B1 | 7/2001 | Treu et al. |
| 6,261,312 B1 | 7/2001 | Dobak, III et al. |
| 6,264,680 B1 | 7/2001 | Ash |
| 6,287,326 B1 | 9/2001 | Pecor |
| 6,290,717 B1 | 9/2001 | Philips |
| 6,299,599 B1 | 10/2001 | Pham et al. |
| 6,304,776 B1 | 10/2001 | Muntermann |
| 6,312,452 B1 | 11/2001 | Dobak, III et al. |
| 6,336,910 B1 | 1/2002 | Ohta et al. |
| 6,338,727 B1 | 1/2002 | Noda et al. |
| 6,368,304 B1 | 4/2002 | Aliberto et al. |
| 6,375,674 B1 | 4/2002 | Carson |
| 6,379,331 B2 | 4/2002 | Barbut et al. |
| 6,405,080 B1 | 6/2002 | Lasersohn et al. |
| 6,409,699 B1 | 6/2002 | Ash |
| 6,419,643 B1 | 7/2002 | Shimada et al. |
| 6,436,295 B2 | 8/2002 | Kim |
| 6,447,474 B1 | 9/2002 | Balding |
| 6,450,990 B1 | 9/2002 | Walker et al. |
| 6,451,045 B1 | 9/2002 | Walker et al. |
| 6,458,150 B1 | 10/2002 | Evans et al. |
| 6,460,544 B1 | 10/2002 | Worthen |
| 6,461,379 B1 | 10/2002 | Carson et al. |
| 6,480,257 B2 | 11/2002 | Cassidy et al. |
| 6,497,721 B2 | 12/2002 | Ginsburg et al. |
| 6,520,933 B1 | 2/2003 | Evans et al. |
| 6,529,775 B2 | 3/2003 | Whitebook et al. |
| 6,530,945 B1 | 3/2003 | Noda et al. |
| 6,530,946 B1 | 3/2003 | Noda et al. |
| 6,547,811 B1 | 4/2003 | Becker et al. |
| 6,551,302 B1 | 4/2003 | Rosinko et al. |
| 6,554,797 B1 | 4/2003 | Worthen |
| 6,572,640 B1 | 6/2003 | Balding et al. |
| 6,579,496 B1 | 6/2003 | Fausset et al. |
| 6,581,403 B2 | 6/2003 | Whitebook et al. |
| 6,582,398 B1 | 6/2003 | Worthen et al. |
| 6,585,692 B1 | 7/2003 | Worthen |
| 6,592,577 B2 | 7/2003 | Abboud et al. |
| 6,592,612 B1 | 7/2003 | Samson et al. |
| 6,602,243 B2 | 8/2003 | Noda |
| 6,620,187 B2 | 9/2003 | Carson et al. |
| 6,620,189 B1 | 9/2003 | Machold et al. |
| 6,635,053 B1 | 10/2003 | Lalonde et al. |
| 6,641,602 B2 | 11/2003 | Balding |
| 6,641,603 B2 | 11/2003 | Walker et al. |
| 6,645,232 B2 | 11/2003 | Carson |
| 6,645,234 B2 | 11/2003 | Evans et al. |
| 6,648,905 B2 | 11/2003 | Hoglund et al. |
| 6,660,027 B2 | 12/2003 | Gruszecki et al. |
| 6,669,715 B2 | 12/2003 | Hoglund et al. |
| 6,673,098 B1 | 1/2004 | Machold et al. |
| 6,676,409 B2 | 1/2004 | Grant |
| 6,676,689 B2 | 1/2004 | Dobak, III et al. |
| 6,682,551 B1 | 1/2004 | Worthen et al. |
| 6,685,733 B1 | 2/2004 | Dae et al. |
| 6,692,518 B2 | 2/2004 | Carson |
| 6,692,519 B1 | 2/2004 | Hayes, Jr. |
| 6,695,873 B2 | 2/2004 | Dobak, III et al. |
| 6,695,874 B2 | 2/2004 | Machold et al. |
| 6,699,267 B2 | 3/2004 | Voorhees et al. |
| 6,699,268 B2 | 3/2004 | Kordis et al. |
| 6,702,842 B2 | 3/2004 | Dobak, III et al. |
| 6,704,590 B2 | 3/2004 | Haldeman |
| 6,706,060 B2 | 3/2004 | Tzeng et al. |
| 6,709,448 B2 | 3/2004 | Walker et al. |
| 6,716,236 B1 | 4/2004 | Tzeng et al. |
| 6,719,724 B1 | 4/2004 | Walker et al. |
| 6,733,517 B1 | 5/2004 | Collins |
| 6,740,109 B2 | 5/2004 | Dobak, III |
| 6,743,218 B2 | 6/2004 | Maginot et al. |
| 6,746,474 B2 | 6/2004 | Saadat |
| 6,749,625 B2 | 6/2004 | Pompa et al. |
| 6,752,786 B2 | 6/2004 | Callister |
| 6,764,391 B1 | 7/2004 | Grant et al. |
| 6,796,995 B2 | 9/2004 | Pham et al. |
| 6,799,063 B2 | 9/2004 | Carson |
| 6,800,068 B1 | 10/2004 | Dae et al. |
| 6,802,855 B2 | 10/2004 | Ellingboe et al. |
| 6,807,444 B2 | 10/2004 | Tu et al. |
| 6,811,551 B2 | 11/2004 | Dae et al. |
| 6,818,012 B2 | 11/2004 | Ellingboe |
| 6,819,950 B2 * | 11/2004 | Mills .......................... 600/322 |
| 6,827,728 B2 | 12/2004 | Ellingboe et al. |
| 6,827,898 B1 | 12/2004 | Fausset et al. |
| 6,872,222 B2 | 3/2005 | Luo et al. |
| 6,878,156 B1 | 4/2005 | Noda |
| 6,887,262 B2 | 5/2005 | Dobak, III et al. |
| 6,887,263 B2 | 5/2005 | Bleam et al. |
| 6,893,454 B2 | 5/2005 | Collins |
| 6,921,198 B2 | 7/2005 | Gruszecki et al. |
| 6,974,463 B2 | 12/2005 | Magers et al. |
| 6,981,945 B1 | 1/2006 | Sarvazyal et al. |
| 7,001,418 B2 | 2/2006 | Noda |
| 7,008,444 B2 | 3/2006 | Dae et al. |
| 7,018,399 B2 | 3/2006 | Dobak, III et al. |
| 7,063,718 B2 | 6/2006 | Dobak, III |
| 7,070,612 B1 | 7/2006 | Collins et al. |
| 7,077,825 B1 | 7/2006 | Stull |
| 7,090,792 B1 | 8/2006 | Balding et al. |
| 7,097,657 B2 | 8/2006 | Noda et al. |
| 7,144,407 B1 | 12/2006 | Lasersohn |
| 7,172,586 B1 | 2/2007 | Dae et al. |
| 7,181,927 B2 | 2/2007 | Collins et al. |
| 7,255,709 B2 | 8/2007 | Walker et al. |
| 7,276,046 B1 | 10/2007 | Suzuki et al. |
| 7,278,984 B2 | 10/2007 | Noda et al. |
| 7,287,398 B2 | 10/2007 | Noda et al. |
| 7,294,142 B2 | 11/2007 | Dobak, III et al. |
| 7,300,453 B2 | 11/2007 | Yon |
| 7,311,724 B1 | 12/2007 | Ginsburg |
| 7,311,725 B2 | 12/2007 | Dobak, III |
| 7,361,186 B2 | 4/2008 | Voorhees et al. |
| 7,371,254 B2 | 5/2008 | Dobak, III |
| 7,407,487 B2 | 8/2008 | Dae et al. |
| 7,425,216 B2 | 9/2008 | Collins |
| 7,458,984 B2 | 12/2008 | Yon et al. |
| 7,491,223 B2 | 2/2009 | Lasheras |
| 7,566,341 B2 | 7/2009 | Keller et al. |
| 7,640,768 B2 | 1/2010 | Noda et al. |
| 7,666,213 B2 | 2/2010 | Freedman, Jr. et al. |
| 7,666,215 B2 | 2/2010 | Callister et al. |
| 7,713,241 B2 | 5/2010 | Cartledge et al. |
| 7,771,460 B2 | 8/2010 | Ginsburg et al. |

| | | | |
|---|---|---|---|
| 7,819,835 B2 | 10/2010 | Landy et al. | |
| 7,824,436 B2 | 11/2010 | Barbut et al. | |
| 2002/0026094 A1 | 2/2002 | Roth | |
| 2002/0033181 A1 | 3/2002 | Groth et al. | |
| 2003/0131844 A1* | 7/2003 | Kumar et al. | 128/200.24 |
| 2003/0135087 A1* | 7/2003 | Hickle et al. | 600/26 |
| 2004/0087606 A1 | 5/2004 | Voorhees et al. | |
| 2004/0102826 A1 | 5/2004 | Lasheras et al. | |
| 2004/0122353 A1 | 6/2004 | Shahmirian et al. | |
| 2004/0138701 A1 | 7/2004 | Haluck | |
| 2004/0158119 A1* | 8/2004 | Osorio et al. | 600/9 |
| 2004/0193098 A1 | 9/2004 | Wentling et al. | |
| 2004/0231664 A1* | 11/2004 | Lurie et al. | 128/200.11 |
| 2005/0033391 A1 | 2/2005 | Worthen et al. | |
| 2005/0177212 A1* | 8/2005 | Njemanze | 607/104 |
| 2005/0203598 A1 | 9/2005 | Becker et al. | |
| 2006/0064146 A1 | 3/2006 | Collins | |
| 2006/0161107 A1* | 7/2006 | Mantle | 604/113 |
| 2006/0190066 A1 | 8/2006 | Worthen | |
| 2006/0276864 A1 | 12/2006 | Collins | |
| 2006/0293734 A1 | 12/2006 | Scott et al. | |
| 2007/0045188 A1 | 3/2007 | Blanton | |
| 2007/0051409 A1 | 3/2007 | Landy, III et al. | |
| 2007/0106247 A1* | 5/2007 | Burnett et al. | 604/508 |
| 2007/0173755 A1* | 7/2007 | Alimi et al. | 604/29 |
| 2007/0203552 A1 | 8/2007 | Machold et al. | |
| 2007/0225781 A1 | 9/2007 | Saadat et al. | |
| 2008/0045867 A1 | 2/2008 | Jensen et al. | |
| 2008/0077088 A1 | 3/2008 | Collins | |
| 2008/0077206 A1 | 3/2008 | Collins | |
| 2008/0119757 A1 | 5/2008 | Winter | |
| 2008/0119788 A1 | 5/2008 | Winter | |
| 2008/0234619 A1 | 9/2008 | Fausset et al. | |
| 2008/0255644 A1 | 10/2008 | Carson | |
| 2009/0099629 A1 | 4/2009 | Carson et al. | |
| 2009/0131835 A1 | 5/2009 | Voorhees et al. | |

FOREIGN PATENT DOCUMENTS

| | | |
|---|---|---|
| WO | WO 93/13718 A1 | 7/1993 |
| WO | WO 98/04191 A1 | 2/1998 |
| WO | WO 00/48670 A1 | 8/2000 |
| WO | WO 00/72779 A2 | 12/2000 |
| WO | WO 01/03606 A2 | 1/2001 |
| WO | WO 01/17471 A1 | 3/2001 |
| WO | WO 01/39819 A2 | 6/2001 |
| WO | WO 01/41708 A2 | 6/2001 |
| WO | WO 01/58509 A1 | 8/2001 |
| WO | WO 02/26175 A1 | 4/2002 |
| WO | WO 02/26176 A1 | 4/2002 |
| WO | WO 02/26285 A2 | 4/2002 |
| WO | WO 02/26307 A1 | 4/2002 |
| WO | WO 02/058606 A1 | 8/2002 |
| WO | WO 03/059218 A1 | 7/2003 |
| WO | WO 2006/060514 A1 | 6/2006 |
| WO | WO 2009/071094 A2 | 6/2009 |
| WO | WO 2009/071096 A2 | 6/2009 |
| WO | WO 2009/071097 A1 | 6/2009 |
| WO | WO 2009/071098 A2 | 6/2009 |
| WO | WO 2009071095 A2 | 6/2009 |

OTHER PUBLICATIONS

Demling, R.H., L. DeSanti, and D.P. Orgill. (2004) Initial management of burn patient. From Burnsurgery.org.*
Rutherford, E.J., D.A. Skeete, and K.J. Brasel. (2004). Management of the patient with an open abdomen: Techniques in temporary and definitive closure. Curr Probl Surg 41: 821-876.*
Sieh, K.-M., K.-M. Chu, and J. Wong. (2001). Intra-abdominal hypertension and abdominal compartment syndrome. Langenbeck's Arch Surg 386: 53-61.*
Hwang, J.C.F., L.H. Hanowell, and C.M. Grande. (1996). Peri-operative concerns in thoracic trauma. Baillière's Clinical Anaesthesiology 10(1): 123-153.*
Stover, J.F., P. Steiger, and R. Stocker. (2005). Treating intracranial hypertension in patients with severe traumatic brain injury during neurointensive care. European Journal of Trauma 2005(4): 308-330.*
Sedlak. (1995). Hypothermia in Trauma: The Nurse's Role in Recognition, Prevention, and Management. International Journal of Trauma Nursing 1(1): 19-26.*
Sieh, J.M., K.M. Chu, and J. Wong. (2001). Intra-abdominal hypertension and abdominal compartment syndrome. Langenbeck's Arch Surg 386: 53-61.*
Rutherford, E.J. et al (2004). Management of the patient with an open abdomen: Techniques in temporary and definitive closure. Curr Probl Surg 41:821-876.*
Sieh, J.M. et al (2001). Intra-abdominal hypertension and abdominal compartment syndrome. Langenbeck's Arch Surg 386: 53-61.*
Sedlak. (1995). Hypothermia in Trauma: The Nurse's Role in Recognition, Prevention, and Management. Int Jrn of Trauma Nursing 1(1): 19-26.*
Demling, R.H. et al (2004) Initial managment of burn patient. From Burnsurgery.org.*
Polderman, K.H. et al (2002). Effects of therapeutic hypothermia on intracranial pressure and outcome in patients with severe head injury. Intensive Care Med 28:1563-1573.*
Hwang, J.C.F. et al (1996). Peri-operative concerns in thoracic trauma. Baillière's Clinical Anaesthesiology 10(1): 123-153.*
Stover, J.F., et al (2005). Treating intracranial hypertension in patients with severe traumatic brain injury during neurointensive care. Euro Jrn of Trauma. 2005(4): 308-330.*
Davison et al.; Epidural cooling for regional spinal cord hypothermia during thoracoabdominal aneurysm repair; J. Vasc. Surg.; vol. 20(2); No. 304-310; Aug. 1994 (Abstract Only).
Burnett et al.; U.S. Appl. No. 12/098,355 entitled "Device and method for safe access to a body cavity," filed Apr. 4, 2008.
Burnett et al.; U.S. Appl. No. 12/169,566 entitled "Hypothermia devices and methods," filed Jul. 8, 2008.
Burnett et al.; U.S. Appl. No. 12/615,045 entitled "Devices and Methods for Monitoring Core Temperature and an Intraperitoneal Parameter," filed Nov. 9, 2009.
Hall et al.; U.S. Appl. No. 12/702,165 entitled "Method and Apparatus for Inducing Therapeutic Hypothermia," filed Feb. 8, 2010.
Mantle, Ross E.; U.S. Appl. No. 12/916,076 entitled "Device for the extravascular recirculation of fluid in body cavities," filed Oct. 29, 2010.

* cited by examiner

US 8,100,880 B2

AUTOMATED THERAPY SYSTEM AND METHOD

CROSS-REFERENCE TO RELATED APPLICATION

This application claims the benefit of U.S. Provisional Patent Application No. 60/921,974, filed Apr. 5, 2007 to Burnett, entitled "Safety Access Device, Fluid Output Monitor & Peritoneal Organ Preservation", the disclosure of which is incorporated by reference herein in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Fluids and other substances are infused into patients for a variety of reasons. For example, fluids may be given to a patient intravenously to hydrate the patient or to control overall blood volume.

It is often important to control infusion of fluid into patients in order to optimize the therapy being provided. Monitoring of patient parameters can consume precious health care time and resources, however. Fluid infusion into patients is therefore not always optimized.

Mantle US 2006/0161107 describes a system that extracts fluid from a body cavity, processes the fluid and then recirculates fluid back into the cavity. Mantle does not describe infusion of a fluid into a patient without extraction of the fluid from the patient, however. In addition, the parameters on which the Mantle system is controlled are limited.

SUMMARY OF THE INVENTION

One aspect of the invention provides an automated therapy system having an infusion catheter; a sensor adapted to sense a patient parameter; and a controller communicating with the sensor and programmed to control flow output from the infusion catheter into a patient based on the patient parameter without removing fluid from the patient. In some embodiments, the sensor may be incorporated into the catheter, and in other embodiments, the sensor may be separate from the catheter. The sensor may be, e.g., an ECG sensor; an EEG sensor; a pulse oximetry sensor; a blood pressure sensor; a cardiac output sensor; a thermodilution cardiac output sensor; a cardiac stroke volume sensor; a heart rate sensor; a blood flow sensor; a pH sensor; a blood $pO_2$ sensor; an intracranial pressure sensor; and/or a solute sensor.

In embodiments of the invention, the catheter may be a peripheral venous catheter; a central venous catheter; an arterial catheter; or a peritoneal catheter (possibly incorporating an intraperitoneal pressure sensor).

Another aspect of the invention provides a method of controlling infusion of a fluid to a patient. The method includes the following steps: monitoring a patient parameter with a sensor to generate a sensor signal; providing the sensor signal to a controller; and adjusting fluid flow to the patient based on the sensor signal without removing fluid from the patient. In some embodiments, the method includes the step of monitoring cardiac output with the sensor and, possibly, adjusting fluid flow to the patient based on cardiac output monitored by the sensor. In embodiments of the invention, the patient parameter includes an electrocardiogram; an electroencephalogram; blood oxygen saturation; blood pressure; cardiac output; cardiac stroke volume; heart rate; blood flow; total circulating blood volume; whole body oxygen consumption; pH; blood $pO_2$; osmolarity; peritoneal cavity compliance; intrathoracic pressure; bladder pressure; and/or rectal pressure.

In some embodiments, the adjusting step includes the step of adjusting fluid flow to achieve or maintain patient euvolumia; adjusting flow of a therapeutic agent (such as a chilled medium) to the patient; adjusting fluid flow to the patient through a peripheral venous catheter; adjusting fluid flow to the patient through a central venous catheter; adjusting fluid flow to the patient through an arterial catheter; and/or adjusting fluid flow to the patient's peritoneal cavity.

Yet another aspect of the invention provides a method of treating hypotension in a patient. The method includes the following steps: monitoring a patient parameter (such as blood pressure or cardiac output) with a sensor to generate a sensor signal; providing the sensor signal to a controller; and adjusting fluid flow to the patient based on the sensor signal without removing fluid from the patient.

Still another aspect of the invention provides a method of treating sepsis in a patient. The method includes the following steps: monitoring a patient parameter (such as blood pressure, central venous pressure, or cardiac output) with a sensor to generate a sensor signal; providing the sensor signal to a controller; and adjusting fluid flow to the patient based on the sensor signal without removing fluid from the patient. Prevention of hypotension and/or hypovolemia is critical in the care of patients that have suffered severe hemorrhage or are septic. These patients are very difficult to monitor and treat, taking significant nursing time and still resulting in suboptimal therapy due to the intermittent nature of the blood pressure, central venous pressure and/or cardiac output checks. The present invention, then, will optimize fluid flow to the patient while also freeing up the already over-taxed nursing staff for other duties.

Yet another aspect of the invention provides a method of inducing and reversing therapeutic hypothermia in a patient. The method includes the steps of: monitoring intracranial pressure to generate a sensor signal; providing the sensor signal to a controller; and adjusting rate of hypothermia induction or rewarming based on intracranial pressure (such as by adjusting fluid flow to the patient), or depth of hypothermia, based on the sensor signal.

In some embodiments of the invention, irrigation and/or lavage of bodily tissues, cavities or spaces (or other patient interventions) may be optimized using a sensor or sensors to report electrical, chemical, acoustic, mechanical properties, pressure, temperature, pH or other parameters surrounding the access device in order to automate and optimize the irrigation/lavage.

Embodiments of the invention include a peritoneal catheter containing one or more sensors which may detect changes in electrocardiograph monitoring, electroencephalograph monitoring, pulse oximetry (either internally or peripherally), peritoneal cavity compliance, intrathoracic pressure, intraperitoneal pressure, intraperitoneal pressure waveforms, bladder pressure, rectal pressure, cardiac output, cardiac stroke volume, cardiac rate, blood flow (e.g., in superior mesenteric, celiac, renal or other arteries), pressure in veins (particularly the inferior vena cava or those that empty into the inferior vena cava, e.g., femoral vein), pressure in arteries (particularly those distal to the aorta, e.g., the femoral artery), total circulating blood volume, blood oxygenation (e.g., in rectal mucosa, peripheral fingers and toes, etc.), whole body oxygen consumption, pH and/or arterial $pO_2$ (or any other parameter that shows a measurable change with increased peritoneal pressure) to ensure safety of automated or manual peritoneal lavage. The invention also includes methods of performing peritoneal lavage using such devices.

Embodiments of the invention include an intravascular catheter containing one or more sensors which may detect changes in electrocardiograph monitoring, electroencephalograph monitoring, pulse oximetry (either internally or peripherally), partial pressure of oxygen or $CO_2$, pH, temperature, blood pressure, central venous pressure, cardiac output, cardiac stroke volume, cardiac rate, blood flow (e.g., in superior mesenteric, celiac, renal or other arteries), total circulating blood volume, pressure in veins (particularly those that empty into the inferior vena cava, e.g., femoral vein), pressure in arteries (particularly those distal to the aorta, e.g., the femoral artery), blood oxygenation (e.g., in rectal mucosa, peripheral fingers and toes, etc.), whole body oxygen consumption, pH and/or arterial $pO_2$ (or any other parameter that shows a measurable change with intravascular volume overload) to ensure safety of manual or automated intravascular infusion. The invention also includes methods of using such devices.

Other embodiments of the invention include control of the rate of infusion to minimize negative effects observed by the sensors. The invention may be used to induce and/or maintain hypothermia or hyperthermia; maximize hydration and/or intravascular volume in a patient receiving intravenous fluids (such as, e.g., post-operative patients, post-hemorrhage patients, septic patients or other intensive care patients).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
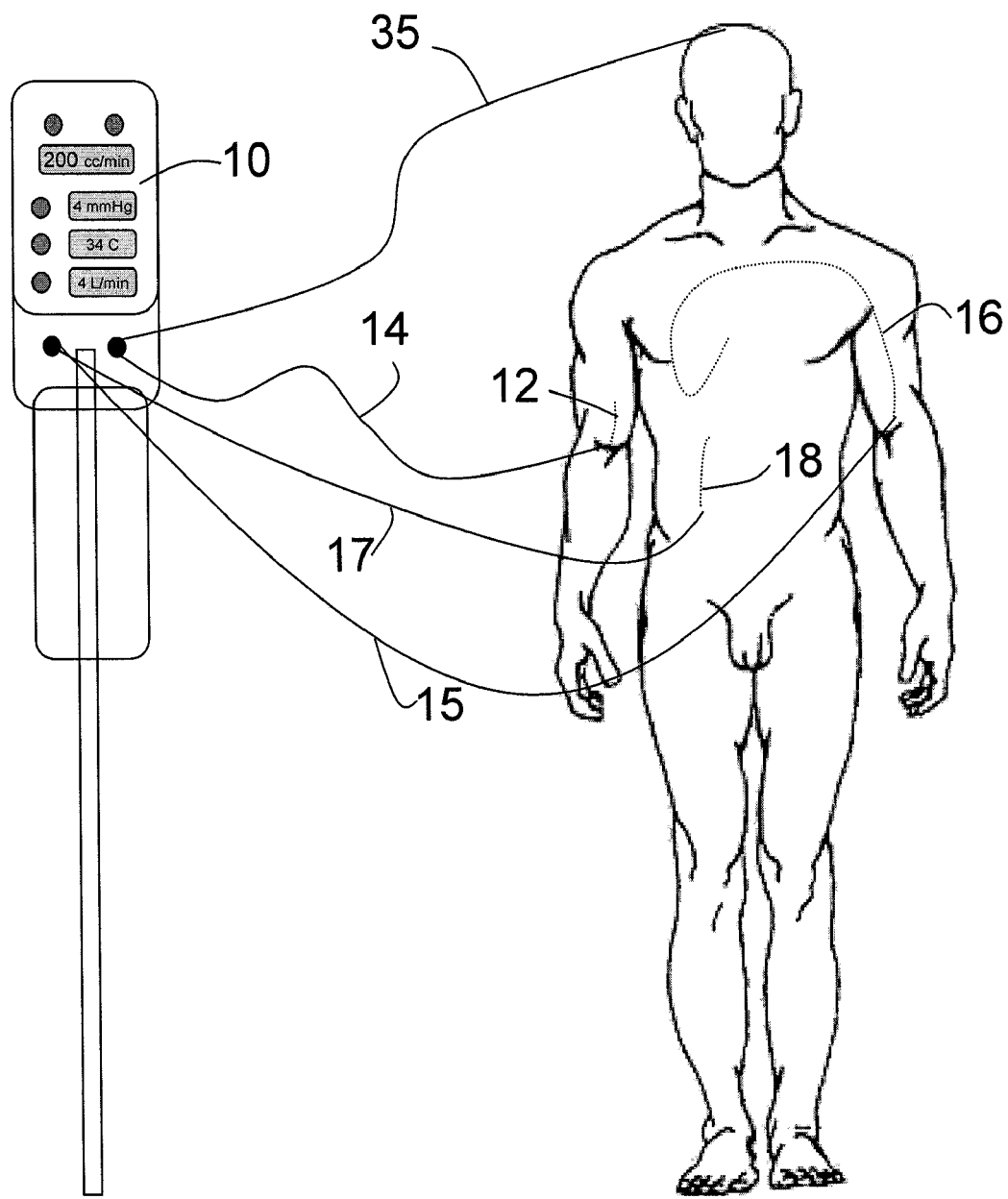
FIG. 1 shows an automated infusion system in which infusion is controlled based on patient parameters sensed by multiple sensors.
Figure 2:
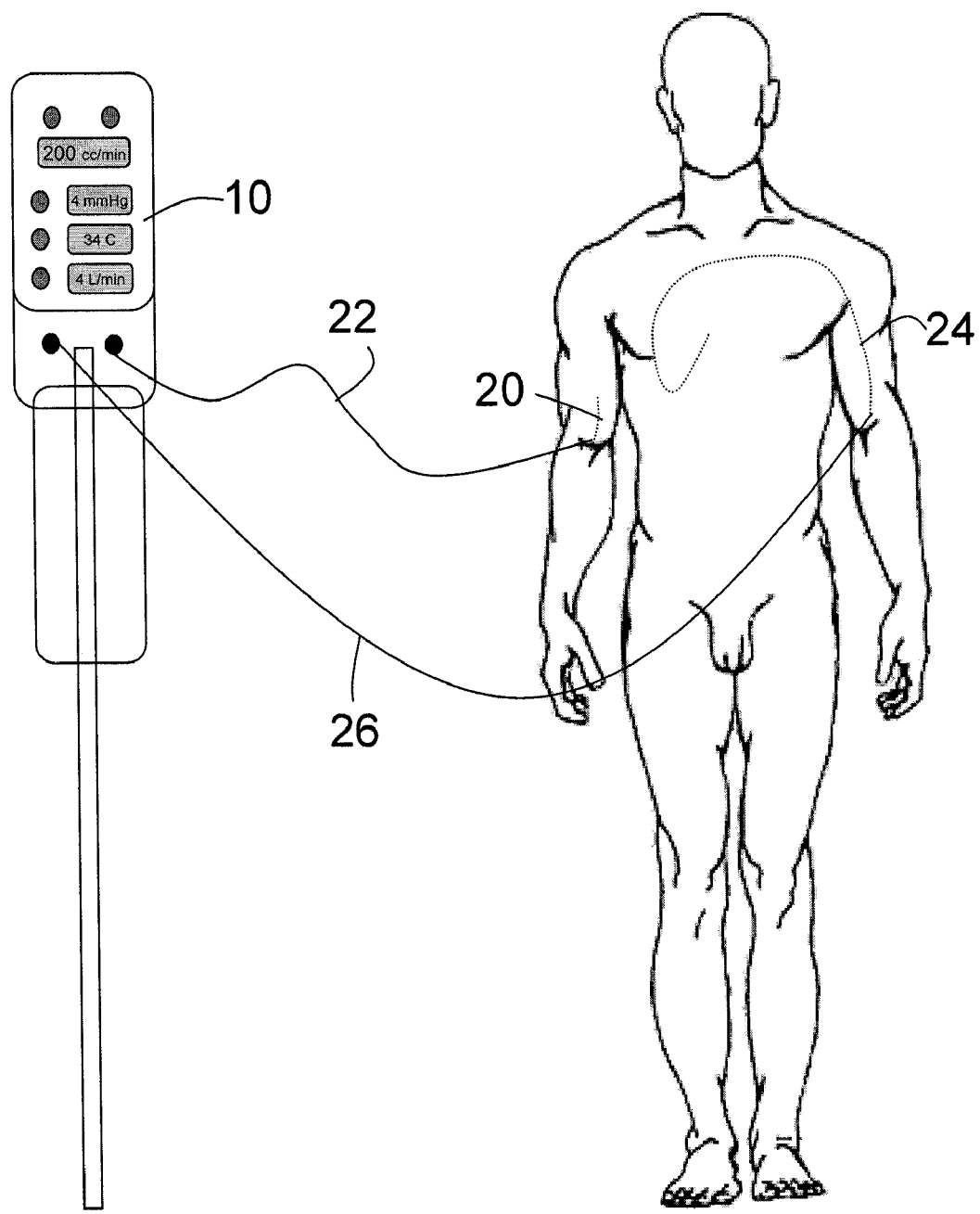
FIG. 2 shows an automated infusion system in which a sensor controlling infusion is separate from the infusion catheter.
Figure 3:
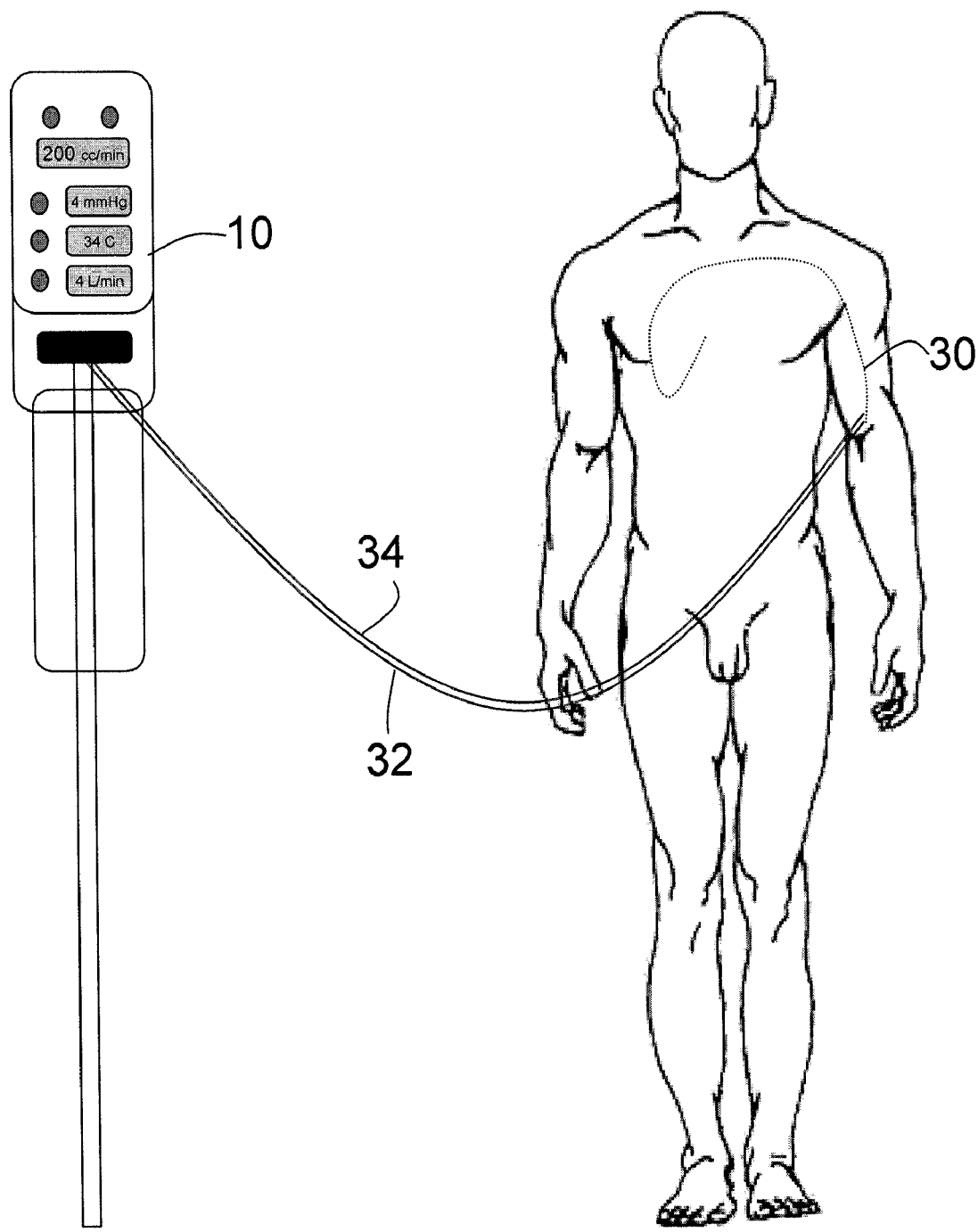
FIG. 3 shows an automated infusion system in which sensing and infusion are performed with the same catheter.

FIGS. 1-3 show embodiments of the invention wherein intravenous fluid delivery may be automated, or manually adjusted, based on feedback from one or more sensors. In these embodiments, the infusion catheter may have a sensor to aid in insertion, but this is not necessary for this invention.

In one embodiment, the infusion catheter also is used to detect the parameters used to optimize therapy. FIG. 1 shows an infusion system with an infusion controller 10 operably connected to an intravenous infusion catheter 12 via an infusion line 14. Infusion catheter 12 also has a sensor (not shown) attached to or associated with it to monitor a patient parameter. The sensor also communicates with controller 10 either through line 14 or via some other communication channel. Suitable patient parameters include electrocardiograph monitoring, electroencephalograph monitoring, pulse oximetry (either internally or peripherally), blood pressure, central venous pressure, cardiac output, cardiac stroke volume, cardiac rate, blood flow (e.g., in superior mesenteric, celiac, renal or other arteries), total circulating blood volume, pressure in veins (particularly those that empty into the inferior vena cava, e.g., femoral vein), pressure in arteries (particularly those distal to the aorta, e.g., the femoral artery), blood oxygenation (e.g., in rectal mucosa, peripheral fingers and toes, etc.), whole body oxygen consumption, pH, arterial $pO_2$, or any other parameter that shows a measurable change with intravascular volume overload.

As shown in FIG. 1, additional catheters, here envisioned as a peripherally inserted central catheter (PICC) 16 and/or a peritoneal catheter 18, or additional sensors on infusion catheter 12 may be used to monitor these or other parameters, and to optimize the infusion rate and achieve euvolemia without fluid overload or dehydration. Flow of fluid and/or a fluid/solid mixture (e.g. an ice slurry) to catheters 16 and/or 18 is controlled by controller 10 through lines 14, 15 and/or 17, respectively. The information from the sensors may then be transmitted to central controller 10, which integrates all of this information to determine the flow of intravenous fluid through catheter 12 and/or catheter 16 and flow of peritoneal fluid through catheter 18. This information may be used to achieve or maintain euvolemia (e.g., in sepsis, hemorrhagic shock, etc.) or to maximize infusion for delivery of a therapeutic agent, e.g., chilled fluid and/or solids to achieve hypothermia. Alternatively, catheters 16 and 18 may be used with sensors to obtain patent information, and fluid may be infused into the patient solely through catheter 16 or catheter 18. In yet further embodiments, the depth of hypothermia and/or rate of hypothermia induction or rewarming may be tailored based on intracranial pressure sensor(s) (not shown) communicating with controller 10 via communication line 35. This system and method may be used with any method of inducing hypothermia (e.g. cooling blankets, intravascular catheters, intravenous fluid infusion, peritoneal lavage, etc.) so long as the change in temperature, particularly rewarming, is controlled at least in part by an intracranial pressure sensor.

The sensor or sensors, whether cables/catheters or percutaneous monitoring technologies, and whether wired or wireless, may also be separate from the infusion line so long as the information from this sensor or sensors is transferred to the control unit in order to optimize fluid flow. Thus, as shown in FIG. 2, the patient parameter sensor may be associated with PICC 24 and communicate with controller via line 26, and infusion to the patient may be via line 22 and infusion catheter 20, as controlled by controller 10. In some embodiments, of course, sensing and infusion may be performed through a single catheter, such as PICC 30, and controlled by controller 10 through lines 32 and 34, as shown in FIG. 3. In some embodiments, the infusion and monitoring device of the current invention may incorporate an access sensor, such as that described in a concurrently filed and commonly owned patent application, U.S. patent application Ser. No. 12/098,355, filed Apr. 4, 2008, titled "Device and Method For Safe Access to a Body Cavity".

One example of such a device is a peripheral venous, central venous or arterial catheter that is capable of maintaining hydration without causing fluid overload. The catheter may incorporate a sensor that may detect central venous pressure, total circulating blood volume, peripheral venous pressure, cardiac output or osmolarity, and/or solute concentrations (e.g., chloride, sodium, etc.) in order to prevent fluid overload. The sensor may also be external to the catheter, so long as the output of said sensor is capable of controlling fluid flow through the catheter. In this embodiment, fluid flow is controlled by the output of the sensor, which is integrated by a fluid flow control unit which alters the rate of fluid flow based on this output. This embodiment may allow the user to bolus large volumes of fluids or solids into the vascular space in order to rehydrate, induce hypothermia or reverse hypothermia, or deliver a therapeutic agent or maintain blood pressure in sepsis.

In addition, this technology may provide a fully automated mechanism to optimize fluid flow into the vessel without fluid overloading the patient. Without this automated fluid delivery coupled to hemodynamic parameter monitoring, the patient is in danger of dehydration or fluid overload from infusion of fluid into any body cavity. This technology may also be applied to liquid or solid infusion into any body cavity or space in so long as the fluid flow is automated based on feedback from sensors within the body (possibly incorporated into the catheter itself) in order to optimize the volume of infusion.

This device and method of automating fluid flow based on hemodynamic sensor-based feedback may also be used to generate intravenous hypothermia. In its current state, IV hypothermia induction is limited due to concerns of fluid overload. If the hemodynamic parameters of the patient can be measured and fluid flow directly or indirectly controlled based on the output of these measurements, the volume of fluid can be maximized while ensuring hemodynamic instability. In this embodiment, the sensor may be incorporated within the catheter, and fluid flow into the vasculature may be tailored based on central venous pressure, total circulating blood volume, peripheral venous pressure, cardiac output or osmolarity, and/or solute concentrations (e.g., chloride, sodium, etc.) in order to prevent fluid overload.

In one embodiment, the fluid infusion catheter also may function as a thermodilution cardiac output sensor such that the same fluid that is used to generate hypothermia may also be used to detect cardiac output. This information may then be relayed, either directly or indirectly, back to the fluid infusion controller to increase, decrease or even halt fluid flow based on these parameters. For example, if cardiac output is low and venous pressure or total circulating volume is low, the patient has a low circulating volume and large volumes of fluid may be safely delivered. If the cardiac output is normal, fluid may also be safely delivered, but the cardiac output must be monitored to ensure that it does not begin to decrease (an indication of fluid overload). Blood flow, as detected by, for instance, thermodilution may determined in a peripheral vessel as well. These data, while relatively useless on their own in a clinical setting due to variability in peripheral blood flow, may provide a baseline flow profile which may be rechecked over time in order to compare flow within that individual vessel to the baseline flow. Relatively improved flow may be correlated to improved cardiac output, while a relative reduction in flow may be correlated to fluid overload.

This same system may be used to infuse normal fluids or hypothermic fluids to sepsis patients or patients requiring intensive maintenance of their hemodynamic status. Sepsis patients that are aggressively monitored do much better than those that are not. Aggressive monitoring is very nurse-intensive, however. A system that provides automated optimal fluid infusion based on sensed parameters to ensure that fluid overload does not occur and that fluid infusion is not insufficient would be an improvement over current methods of treating sepsis patients. The devices and methods for automated sensor-based input to control fluid flow to a patient may be applicable to a wide range of conditions and should not be limited to the narrow scope of the conditions requiring fluid infusion described here.

The logic controller of the present invention may provide improved safety by monitoring for any of the deleterious changes expected with excess fluid flow, e.g. into the peritoneal cavity or vascular space. Examples of monitored parameters that may signal a warning or automatically result in an adjustment to rate of fluid infusion/extraction and/or fluid temperature include: electrocardiograph monitoring, electroencephalograph monitoring, pulse oximetry (either internally or peripherally), peritoneal cavity compliance, intrathoracic pressure, intraperitoneal pressure, intraperitoneal pressure waveforms, bladder pressure, rectal pressure, cardiac output, cardiac stroke volume, cardiac rate, total circulating blood volume, blood flow (e.g., in superior mesenteric, celiac, renal or other arteries), pressure in veins (particularly those that empty into the IVC, e.g., femoral vein), pressure in arteries (particularly those distal to the aorta, e.g., the femoral artery), blood oxygenation (e.g., in rectal mucosa, peripheral fingers and toes, etc.), whole body oxygen consumption, pH and arterial $pO_2$ and any other parameter that shows a measurable change once the peritoneal or vascular spaces have been overloaded.

These parameters in particular have been found to change with increases in peritoneal pressure, with significantly negative impact on each parameter found at 40 mmHg. Thus, monitoring for these changes in conjunction with a peritoneal infusion catheter of the present invention will allow for even greater safety with peritoneal infusion. These parameters may be measured a variety of ways and the data transmitted either wirelessly or via wires to the logic controller in order to alert the healthcare provider or to automatically adjust the fluid flow/temperature in order to optimize both the flow of the peritoneal fluid and patient safety.

What is claimed is:

1. A method of inducing and reversing therapeutic hypothermia in a patient, the method comprising:
   infusing a therapeutic agent into a peritoneal cavity of the patient to induce or reverse therapeutic hypothermia;
   monitoring a patient parameter with a sensor to generate a sensor signal;
   providing the sensor signal to a controller; and
   adjusting flow of the therapeutic agent to the peritoneal cavity of the patient with the controller based on the sensor signal without removing the therapeutic agent from the patient.

2. The method of claim 1 wherein the therapeutic agent is infused into the patient with a peritoneal catheter.

3. The method of claim 1 wherein the patient parameter comprises intraperitoneal pressure.

4. The method of claim 1 wherein the patient parameter comprises intrathoracic pressure.

5. The method of claim 1 wherein the therapeutic agent comprises a chilled medium.

6. The method of claim 1 wherein the infusing step comprises a peritoneal lavage.

7. The method of claim 1 wherein the adjusting step is performed after the infusing step.

* * * * *